United States Patent [19]

Schlein

[11] Patent Number: 4,637,391
[45] Date of Patent: Jan. 20, 1987

[54] SURGICAL SAW BLADE

[76] Inventor: Allen P. Schlein, 107 Curtis Ter., Fairfield, Conn. 06432

[21] Appl. No.: 847,693

[22] Filed: Apr. 3, 1986

[51] Int. Cl.$^4$ .............................................. A61F 15/02
[52] U.S. Cl. ..................................... 128/317; 30/133; 30/166 R; 30/388
[58] Field of Search .............. 128/317, 91 A; 30/377, 30/133, 347, 355, 166 R, 166 A, 388, 371

[56] References Cited

U.S. PATENT DOCUMENTS

| | | | |
|---|---|---|---|
| 803,498 | 10/1905 | Masland | 128/317 |
| 969,579 | 9/1910 | Waldvogel . | |
| 1,641,505 | 9/1927 | Sayre . | |
| 3,353,266 | 11/1967 | Goolsby | 30/167 |
| 4,461,296 | 7/1984 | Hodge | 128/317 |

OTHER PUBLICATIONS

Brochure of Ortopedia GmbH, Federal Rep. of Germany, describing Electrical Plaster Saw, undated.

Primary Examiner—Michael H. Thaler
Attorney, Agent, or Firm—Spencer E. Olson

[57] ABSTRACT

A saw blade adapted for attachment to a power operated surgical saw having teeth disposed along at least a portion of its periphery and having a centrally located saw connector receiving opening and at least one elongated slot disposed between the central opening and the cutting teeth. A cutting depth stop is releasably secured to one side of the blade and extends perpendicularly outwardly therefrom to be movable to desired adjusted positions along the length of the elongated slot. Adjustment of the position of the stop can be performed without tools and even when the saw blade is hot.

9 Claims, 4 Drawing Figures

SURGICAL SAW BLADE

BACKGROUND OF THE INVENTION

This invention relates to surgical saw blades and, more particularly, to an oscillatory surgical saw blade having an adjustable cutting depth stop for use with a power operated surgical saw.

Various techniques have heretofore been utilized by surgeons in cutting and removing surgical casts made of plaster or, more recently, tougher plastic dressings and casts formed of fiberglass. For this purpose, saw blades either rotary or oscillatory in nature have been utilized with power operated surgical saws which, unless means are provided for limiting the depth of cut, pose a danger to the patient. With the oscillatory type of surgical saw, the saw blade performs short, very quick, oscillating motions along a small circular arc at frequencies between 12,000 and 14,000 oscillations per minute. These very short stroking motions will not produce significant cutting effect as the saw temporarily contacts skin or dressing material, but prolonged contact with the skin can cause abrasion and/or burning. However, there is a considerable cutting effect once the saw gets into contact with solid material, such as a plaster cast. Thus, it is desirable that the saw blade be provided with a stop to limit the depth of cut so as to avoid contact with the body limb or portion that is encompassed by the cast.

An oscillatory electrical plaster saw, Model OK7000 available from Ortopedia, a German company, has a cutting depth stop in the form of a flat metal dish which is secured eccentrically with respect to the saw blade to the connector or shaft of the saw. In assembling the saw blade and depth stop onto the shaft, first the saw blade and then the dish-like depth stop are slid onto the toothed shaft and then secured by tightening a cap screw; firm tightening, which requires a socket head wrench, is imperative to prevent destruction of the teeth of the saw blade. The shaft of the saw passes through an off-center hole in the circular dish-like stop such that the lip of the "dish" serves to set the depth of cut in accordance with the rotational position of the dish relative to the selected arcuate cutting portion of the saw blade. Once assembled, the depth of cut can be adjusted only by loosening the cap screw, which requires a wrench, turning the dish relative to the saw blade, and again firmly tightening the cap screw. The need for a tool, and the necessity of allowing the depth stop to cool before adjustment can be effected, makes this saw very inconvenient to use, particularly when depth adjustment is required during the course of the cast removal procedure.

Another form of cutting depth stop for a surgical saw blade is disclosed in U.S. Pat. No. 4,461,296 wherein guard elements are physically secured, as by welding, to opposite sides of a saw blade, the elements being positioned at a fixed predetermined distance from the saw teeth. The guard element may be symmetrical and concentrically located with respect to the center of the blade to provide a constant limitation to the depth of cut, or may be eccentric and/or nonsymmetrical whereby when in oscillating use, different portions of the blade are capable of different depths of cut. The depth of cut for a particular portion of the blade is not adjusable, and a change in depth of cut can be effected only by the user rotating the power tool and the attached saw in his/her hand.

It is an object of the present invention to provide an improved oscillatory surgical saw blade for use in conjunction with a power operated surgical saw, which blade is designed to permit ready and convenient adjustment of the depth of cut.

Another object of the present invention is to provide an improved oscillatory surgical saw blade for use in conjunction with a power operated surgical saw, which blade is designed to permit adjustment of the depth of cut without disconnecting the blade from the saw and without the need for tools.

SUMMARY OF THE INVENTION

Generally speaking, the present invention relates to an improved oscillatory surgical saw blade for attachment to a power operated surgical saw which comprises a blade portion having teeth disposed along at least a portion of an outer periphery of same and defining a cutting surface, and having a saw connector receiving opening therethrough for securement of the blade to the saw, and a cutting depth stop provided on one side of the blade and adapted to be set at an adjusted distance from the cutting teeth and extending outwardly from the blade in a direction perpendicular to the plane of the blade, the length of the cutting depth stop being sufficient to preclude ingress of the cutting teeth beyond a cutting depth defined by the distance between the cutting teeth and the surface of the stop closest the cutting teeth.

More specifically, adjustability of the cutting depth of the surgical saw blade according to the invention is achieved by providing at least one elongated slot therethrough disposed with its long axes on a radius of the blade portion which extends between the central opening and the cutting surface for receiving a cutting depth stop, the stop comprising a hollow cylindrical metal sleeve surrounding an inner hollow cylindrical sleeve formed of a heat absorbing plastic material and a bolt which extends through the slot from the side of the blade from which the connector of the power operated saw is received and threadably engages the inner sleeve. The inner sleeve thermally insulates the outer sleeve from the saw blade sufficiently to enable the outer sleeve to be handled with the fingers, without protection, so as to permit adjustment of the postion of the stop in the course of a cast cutting operation without having to stop and wait for the blade to cool.

Other objects, features and advantages of the invention, and a better understanding of its construction and operation, will be had from the following detailed description, taken in conjunction with the accompanying drawings.

DESCRIPTION OF PREFERRED EMBODIMENTS

Figure 1:
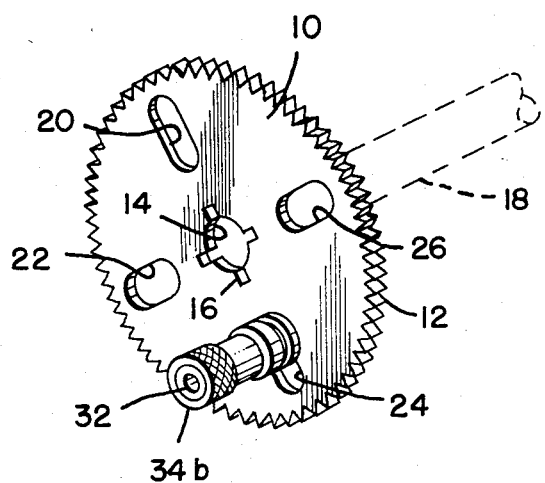
FIG. 1 is a perspective view of a surgical saw blade according to the teachings of the present invention.
Figure 2:
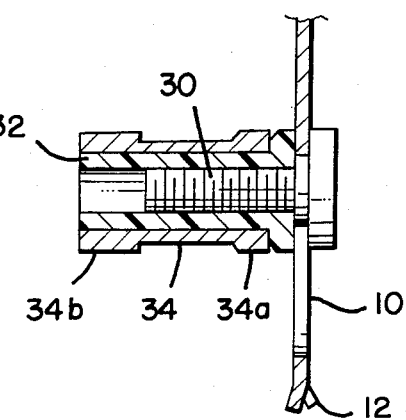
FIG. 2 is an enlarged cross-sectional elevation view of a fragmentary portion of the surgical saw blade shown in FIG. 1.
Figure 3:
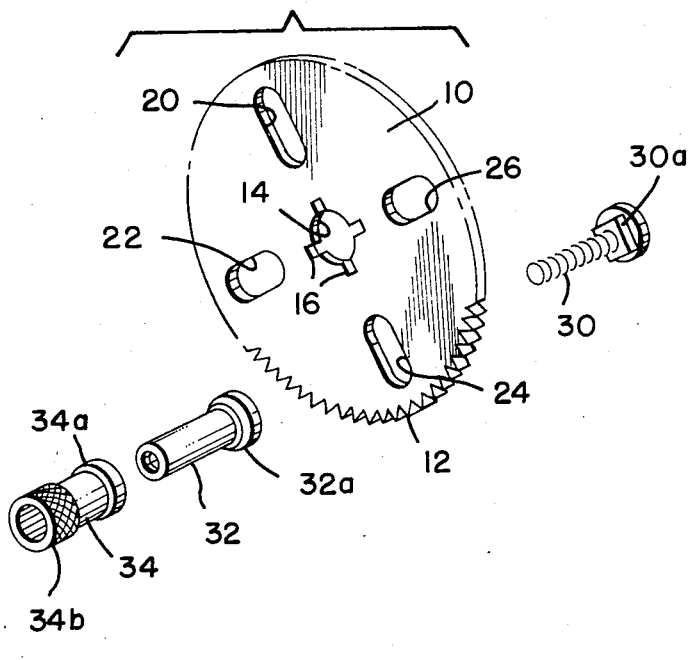
FIG. 3 is an exploded perspective view of the surgical saw blade of FIG. 1.

Referring to the drawings, the embodiment of the improved saw blade shown in FIGS. 1, 2 and 3 is adapted for attachment to a power operated oscillatory saw such as a Stryker saw (not shown) which performs short, very quick oscillating motions on a small circle, typically at between 12,000 and 14,000 oscillations per minute. The blade 10 is circular in shape and has a multiplicity of cutting teeth 12 located around its outer periphery. The blade is provided with a centrally located generally circular opening 14 therethrough, the opening having four key slots 16 extending outwardly from opposite sides thereof, all of which together define a connector receiving opening into which a shaft of a power operated saw, indicated in phantom at 18 in FIG. 1, may be received for securement of the blade to the saw. The four radially extending slots 16 permit the blade 10 to be secured at four different rotational positions relative to the shaft, as the cutting teeth become dulled by cutting a plaster cast or other solid material.

Blade 10 also has four elongated slots 20, 22, 24 and 26 therethrough, the long axes of slots 20 and 24 lying along a diameter of the blade which passes through two of the oppositely extending radial slots, and the axes of slots 22 and 26 lying along a diameter of the saw blade which passes through the other pair of radial slots 16. These slots are all of the same length and are disposed between the central opening 14 and the cutting surface defined by the teeth 12.

The depth of ingress of the cutting teeth is limited by a cutting depth stop which is releasably and adjustably secured in an elongated slot aligned with the selected arcuate cutting portion of the blade, such as slot 24, and extends outwardly and perpendicularly to the side of the blade opposite the side from which the saw connector 18 is received. The cutting depth stop comprises three elements: a hollow cylindrical outer sleeve 34 formed of metal to withstand the abrasion encountered during rapid oscillatory engagement with plaster or fiberglass cast material; a hollow cylindrical inner sleeve 32 formed of a plastics material, such as nylon or Delrin, capable of absorbing heat and the vibration incident to the rapid oscillatory motion of the saw blade; and a carriage bolt 30 having a square head 30a dimensioned to be received between and held against rotation by the edges of slot 24. Inner sleeve 32 is inserted into outer sleeve 34 with a press fit, and to further prevent relative rotation of the inner and outer sleeve, the inner wall of sleeve 34 is preferably fluted or otherwise roughened. The stop is releasably secured to the blade by inserting bolt 30 through slot 24 from the same side as connector 18 is received and threading it into the self-tapping inner sleeve; the square head 30a engaged by the edges of the slot holds the bolt against rotation.

The end of the outer sleeve closest the blade is formed with a shoulder 34a, and the corresponding end of inner sleeve 32 is also formed with a shoulder 32a having approximately the same outer diameter as shoulder 34a such that when assembled, as best seen in FIG. 2, the shoulder 32a engages blade 10 and also separates and thermally insulates the inner end of the metal outer sleeve from the saw blade. Bolt 30 is somewhat shorter than inner sleeve 32 so as to leave an open space beyond the end of the bolt; provision of this space is believed to enhance the transfer to the ambient air of heat conducted by the bolt from the saw, which becomes very hot when cutting a cast. The outer end 34b of the outer sleeve is knurled to facilitate tightening and loosening of the depth stop. Thus, the stop may be easily adjusted to any desired position along the length of slot 24 without tools and without having to remove the blade from the power saw.

The depth stop should extend outwardly from blade portion 10 for a sufficient distance that the surface thereof closest the teeth will engage the cast and preclude further ingress of the cutting teeth into the cast. Typically, the depth stop has a total length in the range from one half inch to three-fourths inch.

Although an oscillatory saw blade becomes too hot to touch after only a relatively short cutting operation, it has been found that the thermal insulation provided by the inner sleeve keeps the temperature of the outer sleeve sufficiently cool to be safely handled by the fingers. Thus, the stop can be conveniently adjusted to different depths during a castcutting operation, without tools, and without having to wait for the blade to cool. This important advantage results from the use of the thermally insulating inner sleeve, the provision of shoulder 32a on the inner sleeve, and making bolt 30 somewhat shorter than the inner sleeve. The shoulder 32a also mechanically isolates the metal outer sleeve from the blade, and since the plastics material is slightly deformable, makes more secure the attachment of the stop to the blade than if the metal sleeve were to engage the blade.

Figure 4:
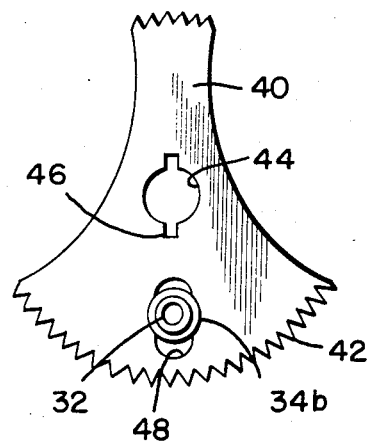
FIG. 4 is an end elevational view of a further embodiment of the present invention, illustrating a cutting depth stop in use with an oscillatory saw blade having a single cutting surface.

FIG. 4 illustrates a further embodiment of the improved saw blade according to the teachings of the invention wherein an oscillatory blade 40 has cutting teeth 42 located along an arcuate section to define a cutting surface therealong. At the terminal portions of the arcuate section the blade extends rearwardly in concave fashion to define a counterbalance blade section. Blade 40 is provided with a saw connector receiving opening 44, also having rectangular key slots 46 extending outwardly from opposite sides thereof for receiving the shaft or connector of a power operated surgical saw, such as an oscillatory Stryker saw. The blade has an elongated slot 48 therethrough disposed with its long axis aligned with rectangular slots 46 in which a depth stop having the above-described construction is releasably secured. Thus, this embodiment affords an adjustable cut depth for a single blade.

Although the invention has been described in detail as to preferred embodiments, it is obvious that certain modifications or alterations may be made thereto without departing from the scope of the invention. For example, although nylon and Delrin have been mentioned as suitable plastics materials for the inner sleeve, it is within the contemplation of the invention that other materials capable of providing suitable thermal insulation and of withstanding the vibration encountered in the operation of oscillatory surgical saws can be used. Also, the circular embodiment may have only two elongated slots for receiving the cutting depth stop, in which case the connector-receiving opening would require only two key slots 16. The connector-receiving opening may also have shapes other than those illustrated; for example, it may have the hexagonal shape used by Martin Medical in its surgical saw blades. Also, a scale may be etched or printed along an edge of each elongated slot to facilitate setting of the stop to a desired depth of cut. The scope of the invention should thus be determined by the claims appended hereto.

I claim:

1. A surgical saw blade for attachment to a power operated oscillatory surgical saw comprising:
   a blade portion having teeth disposed along at least a portion of an outer periphery of same and defining an arcuate cutting surface thereat, said blade portion having a central saw connector-receiving opening therethrough for securement of said blade to said saw, and also having an elongated slot therethrough disposed with its long axis on a radius of said blade portion extending between said central opening and the arcuate cutting surface of said blade portion, and
   a cutting depth stop including a cylindrical metal sleeve surrounding a hollow cylindrical inner sleeve formed of thermal insulating plastics material and extending outwardly from one side of said blade in a direction perpendicular to the plane of said portion and releasably secured at a desired adjusted position along said elongated slot by a bolt extending through said slot from the other side of said blade portion and threadably engaging said cylindrical inner sleeve, the length of said metal sleeve being sufficient to preclude ingress of said cutting teeth beyond a depth defined by the distance between said cutting teeth and a surface of said metal sleeve closest said teeth.

2. A saw blade as defined in claim 1 wherein said blade portion is circular.

3. A saw blade as defined in claim 2, wherein said central opening is generally circular in shape with at least one pair of oppositely positioned slots extending outwardly therefrom, and said blade portion has at least two elongated slots therethrough disposed on opposite sides of said central opening with their long axes lying along a diameter of said blade which passes through said outwardly extending slots.

4. A saw blade as defined in claim 1 wherein the end of said inner sleeve closest said blade is formed with a shoulder having approximately the same outer diameter as said metal sleeve for enhancing the securement of said depth stop to said blade portion and for thermally insulating said metal sleeve from said blade.

5. A saw blade as defined in claim 4 wherein said inner sleeve is formed of Delrin.

6. A surgical saw blade for attachment to a power operated oscillatory surgical saw comprising:
   a circular blade having teeth disposed along the outer periphery of same and defining a cutting surface threat, said blade having a central saw connector-receiving opening therethrough for securement of said blade to said saw and also having a radially oriented elongated slot disposed between said central opening and the cutting surface of said blade, and
   a cutting depth stop extending outwardly from and perpendicularly to the side of said blade opposite the side from which the saw connector is received, said cutting depth stop comprising a cylindrical outer sleeve formed of metal surrounding a hollow cylindrical inner sleeve formed of thermal insulating plastics material, and a bolt extending through said elongated slot from the side of said blade from which the saw connector is received and threadably engaging said inner sleeve for releasably securing said stop at a desired adjusted position along said elongated slot, the length of said outer sleeve being sufficient to limit ingress of said cutting teeth beyond a depth defined by the distance between said cutting teeth and the surface of said outer sleeve closest said teeth.

7. A saw blade as defined in claim 6 wherein the end of said inner sleeve closest said blade is formed with a shoulder having approximately the same outer diameter as said outer sleeve for enhancing the thermal insulation of said outer sleeve from said blade and the securement of said stop to said blade.

8. A saw blade as defined in claim 7 wherein said plastics material is Delrin.

9. A saw blade as defined in claim 7 wherein the central opening in said blade has at least one pair of oppositely positioned slots extending radially outwardly therefrom, and wherein said blade has at least two elongated slots therethrough disposed on opposite sides of said central opening with their long axes lying along a diameter of said blade which passes through said outwardly extending slots.

* * * * *